United States Patent [19]

Linke et al.

[11] Patent Number: 4,966,538

[45] Date of Patent: Oct. 30, 1990

[54] MOUNTING PRESS

[75] Inventors: Thomas A. Linke, Wadsworth; Troy W. Livingston, Northbrook; Christopher D. Wanha, Chicago; Charles E. Shewey, Mundelein, all of Ill.

[73] Assignee: Buehler, Ltd., Lake Bluff, Ill.

[21] Appl. No.: 201,061

[22] Filed: Jun. 1, 1988

[51] Int. Cl.$^5$ ................ B29C 43/58; B29C 33/20
[52] U.S. Cl. .................. 425/144; 264/279;
264/279.1; 264/40.6; 425/112; 425/125;
425/127; 425/128; 425/149; 425/161; 425/167;
425/189; 425/195; 425/186; 425/352; 425/415
[58] Field of Search ........ 425/127, 128, 143, 145–150,
425/161, 167, 170–171, 175–179, 151, 189, 193,
182, 186, 192 R, 110, 117, 407, 406, 351, 352,
195, 412, 415, 416, 423, 78, 384, DIG. 9, DIG.
13; 100/240, 245, 246; 264/279, 279.1, DIG. 46,
40.6

[56] References Cited

U.S. PATENT DOCUMENTS

| | | | |
|---|---|---|---|
| 1,842,406 | 1/1932 | Kattwinkel | 425/415 |
| 2,977,657 | 4/1961 | Willemsen | 425/412 |
| 3,129,463 | 4/1964 | Gill, Jr. et al. | 425/110 |
| 3,141,915 | 7/1964 | Nieuwenhuis et al. | 425/143 |
| 3,206,279 | 9/1965 | Carnall, Jr. | 425/407 |
| 3,226,772 | 1/1966 | Balaguer | 425/DIG. 13 |
| 3,339,227 | 9/1967 | Ehrenfreund | 425/144 |
| 3,458,896 | 8/1969 | Zetterlund et al. | 425/384 |
| 3,488,809 | 1/1970 | James | 425/384 |
| 3,561,058 | 2/1971 | Komendowski | 425/384 |
| 3,596,317 | 8/1971 | Nicholson | 425/128 |
| 3,825,386 | 7/1974 | Belle et al. | 425/150 |
| 3,999,916 | 12/1976 | Hable et al. | 425/352 |
| 4,184,826 | 1/1980 | Reed et al. | 425/110 |
| 4,252,458 | 2/1981 | Keen | 403/320 |
| 4,423,992 | 1/1984 | Ankeny | 411/221 |
| 4,609,338 | 9/1986 | Nishida et al. | 425/149 |
| 4,642,043 | 2/1987 | Schwarzkopf | 425/143 |

FOREIGN PATENT DOCUMENTS

| | | | |
|---|---|---|---|
| 63-28615 | 2/1988 | Japan | 425/150 |
| 725906 | 4/1980 | U.S.S.R. | 425/143 |

Primary Examiner—Jeffery Thurlow
Assistant Examiner—Mathieu Vargot
Attorney, Agent, or Firm—Allegretti & Witcoff, Ltd.

[57] ABSTRACT

Molding apparatus, particularly for mounting specimens for microstructural analysis. A ramhead pressurizes a molding chamber, with the pressure, temperature and time of the cycle being set into the system from a control panel and proceeding automatically. The ramhead is advanced through a hydraulic system. A spring is provided for mounting the tubular molding chamber to permit the molding chamber to spontaneously align with the advancing ramhead. A wrench member is provided as an integral part of the apparatus to rotationally lock the handle to the molding chamber, to permit rotation of the molding chamber through the handle for removal thereof when desired.

17 Claims, 1 Drawing Sheet

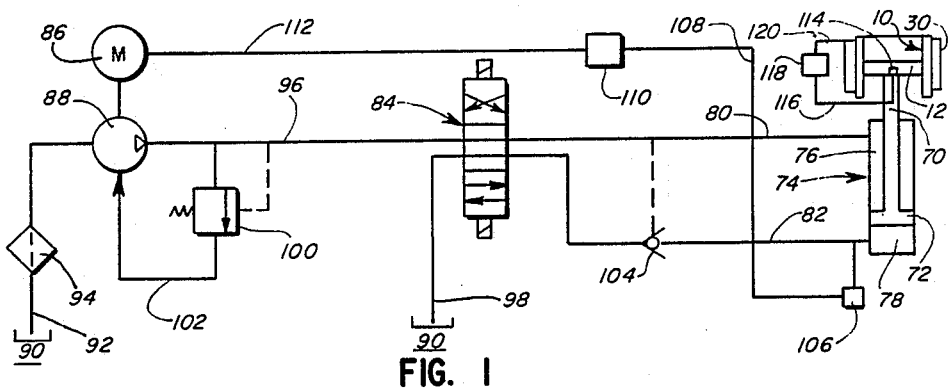
FIG. 1
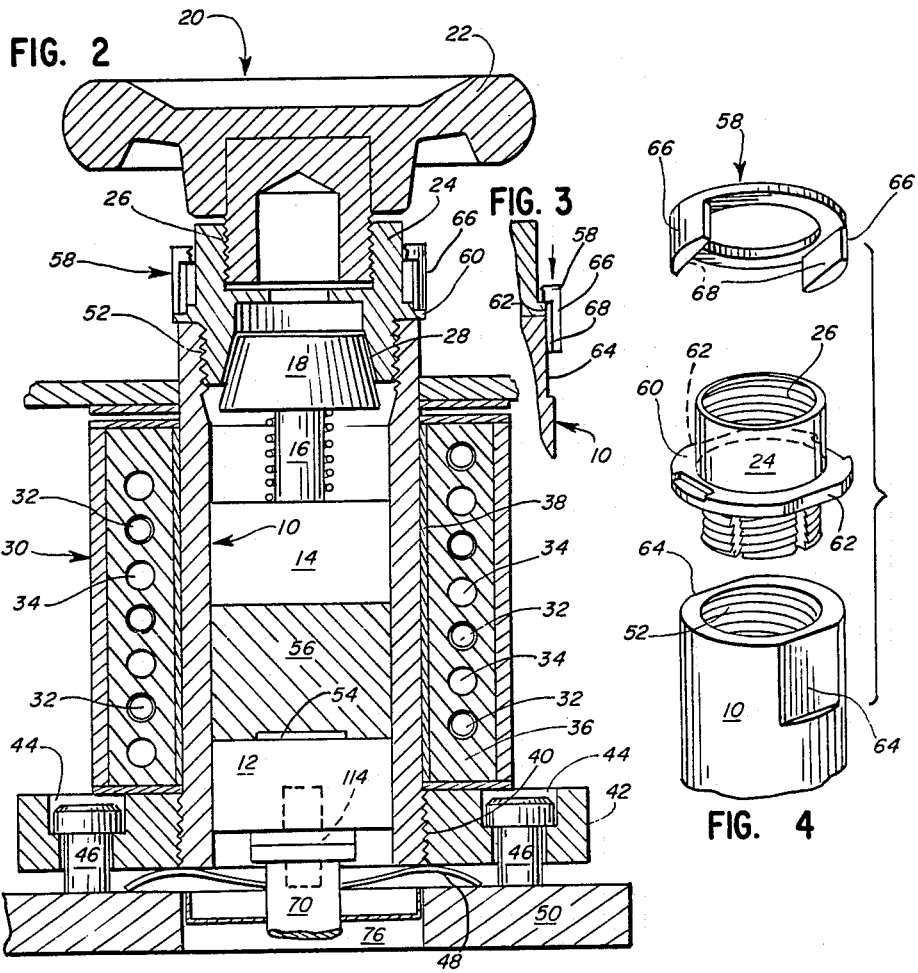
FIG. 2
FIG. 3
FIG. 4

MOUNTING PRESS

BACKGROUND OF THE INVENTION

In the field of microstructural analysis of surfaces, surfaces of metal, minerals, or any other desired surface are cut as a thin wafer, mounted in a plastic block, polished, and microscopically analyzed. The step of mounting the wafer-like sample in plastic permits the easy handling of a very thin wafer of material, and has been performed in the prior art, for example, by the Simplimet II brand of specimen molding press, sold by Buehler Ltd. of Lake Bluff, Illinois. This prior art specimen press carries a cylindrical molding chamber having a ramhead sealingly movable along the length of the chamber to pressurize a mass of plastic which overlies the wafer-like sample to be mounted in the plastic. The prior art unit uses manually pumped pneumatic pressure to drive the piston, while the plastic is heated to melting to form an integral plastic block, with the sample carried on one face of the plastic block.

Such a manual system requires hand pumping to a pressure that is greater than the desired molding pressure, to account for the fact that the plastic molding compound will decrease in volume as the molding proceeds, thus causing a reduction in the pressure. Thus, such a prior art system, while effective in many circumstances, is not as precise in its pressure application as may often be desired, without careful and continuous monitoring.

Also, in prior art specimen mounting presses, it has been necessary to be sure that there is precise, coaxial alignment between the tubular molding chamber and the axis of motion of the ram, in order to avoid scouring and possible damage to the molding chamber or ram. In accordance with this invention, improvements are provided in which automated, precise specimen mounting may be provided, with precise control not only of pressure under the dynamic conditions of molding, but also precise control of molding time and temperature. Similarly, the length of the molding cycle may be shortened according to this invention, while the molding apparatus is adapted to be less subject to damage or binding through misalignment of the tubular molding chamber with the axis of motion of the ram.

DESCRIPTION OF THE INVENTION

The present invention relates to a molding apparatus which comprises a tubular molding chamber having a ramhead sealingly movable along the length of the interior of the chamber. Fluid pressure means are provided for advancing and retracting the ramhead along the chamber.

In accordance with this invention, hydraulic chamber means are also provided. A shaft extends axially from the ramhead into the hydraulic chamber in sealing manner, and terminates in a sliding piston within the hydraulic chamber to divide the hydraulic chamber into a pair of variable volume portions positioned on opposed sides of the piston, the variation of the volume of each of the chamber portions being dependent upon the position of the piston. Each chamber portion is connected by hydraulic flow conduit means to a source of pressurized hydraulic fluid, to permit driven movement of the piston in the chamber. Pressure sensing means are provided, being operably connected to the hydraulic chamber portion which is spaced from the ramhead by the piston. Also, logic and control means are operably connected to the pressure sensing means as well as the pressurized hydraulic fluid source, to control the pressure of hydraulic fluid in the last-named, spaced chamber portion in a manner which is responsive to signals from the pressure sensing means.

Thus, in the apparatus of this invention, the pressure exerted on the mass of molding compound placed in the tubular molding chamber, typically for molding into a solid unit that carries a sample for surface analysis, may be predetermined and uniform, with the logic and control means causing the pressure sensing means to add units of pressure to the molding chamber as necessary to keep the pressure substantially constant as the molding compound shrinks together during the process.

The fluid pressure means may comprise a hydraulic fluid pump (and connected source of hydraulic fluid) connected by a third conduit to double acting, venting valve means. The switch means is, in turn, connected to the hydraulic flow conduits which respectively connect to the variable volume portions on either side of the piston in the hydraulic chamber. As a result of this, switching of the valve means can cause alternative pressurizing and venting of each of the variable volume portions, to operate the piston as desired, and to impose any desired pressure by way of the ramhead in the tubular molding chamber.

The molding chamber can be surrounded by typically separate helical heating and cooling coils, the heating coil typically being an electrical heater, and the cooling coil typically being a conduit for cooling fluid. Temperature measuring means are positioned adjacent to the molding chamber, and control means are provided for operating at least said heating coil in a manner responsive to signals from the temperature measuring means. Typically, the helical heating and cooling coils are both mounted in a single sleeve member and work in alternating manner.

Additionally, the tubular molding chamber may be mounted on resilient means such as a spring member or the like. The effect of this is to permit the molding chamber to spontaneously align with the ramhead as the ramhead moves along the length of the chamber, thus avoiding the need for extremely precise alignment as discussed above.

Additionally, the molding chamber may be threadedly attached to a base member at one end. The opposed end of the molding chamber may carry a handle member, the handle member defining an annular flange having first, spaced, peripheral flat areas. The opposed end of the molding chamber defines second, spaced, peripheral flat areas which are proportioned to enter into longitudinal registery with the first, peripheral, flat areas by proper rotational orientation.

The handle member also carries an annular wrench member which defines third flat areas on an inner annular surface thereof. The wrench member is proportioned to slide over the flange and opposed end, with the third flat areas overlying the first and second flat areas.

As a result of this, the handle can be used to rotate the molding chamber out of threaded attachment with the base member to open the mold, when the wrench member is in its position of engagement with the first and second flat areas. At other times, the wrench member may be lifted out of engagement, and the handle member may be removed from the molding chamber, typically by unscrewing it from its threaded attachment to the opposed end of the molding chamber.

The apparatus of this invention may be used in a wide variety of molding methods. However, preferably, the molding process may be performed with the molding chamber surrounded in heat exchange relation with a heat-conductive metal, tubular heating sleeve. In this method, one heats the heating sleeve to a temperature that exceeds the desired maximum molding temperature of the plastic member within the molding chamber by at least 50° F., while monitoring the temperature of the molding chamber with heat measuring means positioned therein. One then terminates heating of the heating sleeve prior to the temperature of the molding chamber reaching the desired maximum molding temperature. The effect of this is to provide a faster molding process, but at the same time one can reliably achieve the desired maximum molding temperature to achieve the desired molding results.

Preferably, the heating sleeve will also include cooling means, typically of the type described above. The cooling means may be activated prior to the molding chamber reaching the desired maximum molding temperature. By the use of this technique, the molding cycle may be further shortened. Typically, the heating sleeve maximum temperature exceeds the desired maximum molding temperature by 100 to 200 degrees F.

DESCRIPTION OF DRAWINGS

FIG. 1 is a schematic diagram of the molding apparatus of this invention, showing particularly its hydraulic circuit and certain electronic circuits;

FIG. 2 is a longitudinal sectional view of the tubular molding chamber, ramhead, and heating and cooling means of the apparatus of FIG. 1;

FIG. 3 is a fragmentary view similar to FIG. 2 showing the annular wrench member in its locked, operating position; and FIG. 4 is an exploded perspective view of a portion of the structure of FIG. 2.

DESCRIPTION OF SPECIFIC EMBODIMENT

Referring to the drawings, the molding apparatus of this invention includes a tubular molding chamber 10 having a ramhead 12 sealingly movable along the length of the interior of chamber 10. As shown in FIG. 2, chamber 10 also carries second sliding member 14 which is mounted with a spring and shaft assembly 16, to be slidingly movable for certain distance with respect to frustoconical upper base member 18, in a manner similar to corresponding structure in the prior art.

Handle 20 comprises outer handle member 22 and inner handle member 24, which may be threadedly attached to outer handle 22 along threads 26 and then permanently secured together by welding or the like. Inner handle member 24 defines a frustoconical seat 28 to receive frustoconical upper base 18 as shown, base 18 being separable out of seat 28 when the system is opened.

Molding chamber 10 fits in close, sliding manner within heating and cooling sleeve 30. Sleeve 30, in turn, carries a helical array of resistance heating wires 32 and a spaced, helically disposed cooling conduit 34 through which cooling fluid such as cold water may be passed, the two helical arrays 32, 34 having loops that are in alternating relation with each other, as shown. Each of helical arrays 32, 34 may be conventionally connected to their respective source of heating or cooling.

The inner portion 36 of heating and cooling sleeve 30 may be made of aluminum, with an inner copper or brass sleeve 38 being typically provided to promote a high heat transfer interface, and to serve as a more wear resistant surface as various molding chambers 10 are inserted into and withdrawn from the system.

As shown in FIG. 2, molding chamber 10 is carried in movable threaded engagement 40 with loosely attached plate 42, plate 42 being loosely attached at oversized apertures 44 to posts 46. Plate 42 and molding chamber 10 rest upon a conventional wave spring 48 which, in turn, rests upon base 50. As a result of this, molding chamber 10 can be spontaneously and precisely aligned with the advancing ram 12, any misalignment being compensated for by the resilient means used for mounting molding chamber 10.

In the apparatus of this invention, molding chamber 10 may be removed for replacement with another molding chamber of a different inner diameter or the like, or if it is desired to clean or repair molding chamber 10. However, after use, it is sometimes difficult to start the rotation of molding chamber 10 out of its threaded engagement 40 with plate 42. To facilitate this, a novel connection between handle 20 and molding chamber 10 is provided.

Typically, molding chamber 10 and handle 20 are connected together in threaded relation 52. This permits the removal of handle 20 when desired, followed by the removal of members 14, 16, 18, for placing a wafer 54 of material to be mounted in mass of plastic 56. Wafer 54 may be inserted to rest upon ram 12, and then plastic mass 56 added, following which members 14, 16, 18 are applied and handle 20 threaded into its relation as shown in FIG. 2. Again, the same process may take place to remove plastic mass 56, if desired, or, alternatively, it may be more convenient to remove the entire molding chamber 10 for easier access to the molded plastic mass 56 carrying its wafer 54.

Annular wrench member 58 is carried on handle 20, to make possible the use of handle 20 to break the threaded engagement 40 between chamber 10 and plate 42, despite the threaded engagement 52 between handle 20 and molding chamber 10. As shown particularly in FIG. 4, lower portion 24 of handle member 20 defines an annular flange 60 having first, spaced, peripheral flat areas 62 positioned in opposed relation. The upper end of molding chamber 10 defines second, spaced, peripheral flat areas 64, which are proportioned to enter into longitudinal registry with the first, peripheral flat areas 62 by proper rotational orientation, as in FIG. 3. Annular wrench member 58, in turn, defines projections 66 which, in turn, define third flat areas 68, proportioned to slide over flat areas 62, 64 so that flat area 68 overlies flat areas 62, 64. Thus, in the configuration shown in FIG. 3, handle 20 is locked from relative rotation with respect to molding chamber 10 along threads 52. Handle 20 can then be used to apply vigorous torque to molding chamber 10, to break it out of its threaded relation 40 with plate 42 for removal thereof from the apparatus.

Turning particularly to FIG. 1, ram 12 is carried on shaft 70, which terminates in sliding piston 72 within a hydraulic chamber 74, so that sliding piston 72 divides hydraulic chamber 74 into a pair of variable volume portions 76, 78 positioned on opposed sides of piston 72. Each of chamber portions 76, 78 are connected by a hydraulic flow line 80, 82 to a double acting venting valve 84. Such a double acting venting valve is available for example from The Rexroth Corporation.

Motor 86 operates hydraulic pump 88 to draw hydraulic fluid from reservoir 90 through line 92 and filter 94, to be pumped along line 96 as pressurized fluid through valve 84. Depending upon the position of valve 84, the pressurized fluid can move through either line 80 or 82, to pressurize chamber 76 to cause ram 12 to withdraw downwardly, or to pressurize chamber 78 to advance ram 12 to pressurize the plastic material 56 in molding chamber 10. When one of lines 80, 82 is so connected to line 96, the other line is connected through valve 84 with exhaust line 98 so that hydraulic fluid may be returned through that line to reservoir 90. Internal pressure relief valve 100 protects line 96, motor 86, and pump 88 from overload, with recycling circuit 102 being present in a conventional form of hydraulic circuit design. Thus, pump 88 may be continuously operated by motor 86, with valve 84 being operated as necessary to provide the desired direction of pressurization with respect to chamber portions 76, 78. Pilot operated check valve system 104 is provided to prevent leakage while ram 72 is being forced into the mold pressurizing mode, this system being a conventional hydraulic technique.

Transducer 106 monitors pressures in hydraulic line 82 and sends an electronic signal through conductor 108 to a conventional logic and control circuit means 110. Logic control circuit means 110, in turn, may control motor 86 through conductor wire 112 in accordance with predetermined instructions to keep the desired pressure and time of application thereof within chamber portion 78 to the desired parameters, with the result that plastic 56 is pressurized by ram 12 in a manner which may be predetermined by console controls which provide instructions to circuit 110.

Thermistor 114 may be positioned on the rear side of ram 12 to serve as the temperature measuring means positioned adjacent, and preferably within, molding chamber 10, as shown. Thus, a temperature reading may be provided from a location which is spaced from and interior of the heating and cooling coil 30, so that such temperature reading closely approximates the actual temperature of the plastic mass 56, being relatively independent of the temperature which may be recorded in a second thermistor carried on the heating and cooling coil 30.

Thermistor 114 is connected by conductive wire 116 (FIG. 1) to an electronic logic unit 118, which communicates through conductive wire 120 to the heating coil 32 of heating and cooling sleeve 30. Thus, logic unit 118 may be instructed from a control console to maintain a desired temperature reading from thermistor 114 by control of the temperature of heating wires 32.

As a result of this, a molding system is provided in which the temperature, time of molding, and molding pressure may all be set into the system from a control console with confidence that the proper molding cycle as called for will take place.

Particularly, it is preferred in accordance with this invention to heat the heating and cooling sleeve 30 to a maximum temperature in the molding cycle that exceeds the desired maximum molding temperature of the plastic member by typically about 100 to 150 degrees. For example, sleeve 30 may be heated to about 450° F., when using a typical phenolic plastic material 56 which to be molded at 300° F. maximum temperature. In a typical apparatus of this invention for mounting a specimen in a block of plastic of conventional dimensions, the heating step continues for about 3 to 4 minutes at a temperature up to 450° F., followed by shut off of heating through heating coil 32 and the institution of cooling water in cooling coil 34. The entire molding process with its heating and cooling phases runs about 8 to 9 minutes, with heating coil 30 overshooting the desired molding temperature, and them shutting off to permit the maximum temperature in molding chamber 10 to rise, as monitored by thermistor 114, to the desired molding temperature.

After the cooling process is complete, the pressure may be reduced by retraction of ram 12 by operation of valve 84. Handle 20 may then be used to open the system to obtain the mounted specimen 54.

The above has been offered for illustrative purposes only, and is not intended to limit the scope of the invention of this application, which is as defined in the claims below.

That which is claimed:

1. In molding apparatus which comprises a tubular molding chamber; a ramhead sealingly movable along the length of the interior of said chamber; and fluid pressure means for advancing and retracting said ramhead along said chamber; the improvement comprising, in combination:

hydraulic chamber means; a shaft extending axially from said ramhead into said hydraulic chamber in sealing manner and terminating in a sliding piston within said hydraulic chamber to divide said hydraulic chamber into a pair of variable volume portions positioned on opposed sides of said piston, each portion being connectable by hydraulic flow conduit means to a source of pressurized hydraulic fluid, to permit driven movement of said piston in said chamber; pressure sensing means operably connected to the hydraulic chamber portion which is spaced from said ramhead by said piston; and logic and control means operably connected to said pressure sensing means and pressurized hydraulic fluid source to control the pressure of hydraulic fluid in said spaced chamber portion in a manner responsive to signals from said pressure sensing means; said molding chamber being surrounded by a sleeve member, said sleeve member containing spaced, interwinding heating and cooling coils mounted therein; temperature measuring means positioned adjacent said molding chamber; and control means for operating said heating and cooling coils in a manner responsive to signals from said temperature measuring means.

2. The molding apparatus of claim 1 in which said fluid pressure means comprises a hydraulic fluid pump connected by a third conduit to double acting venting valve means connected to the hydraulic flow conduit means which respectively connect to the variable volume portions, whereby switching of said valve means can cause alternating pressurizing and venting of each of said portions.

3. The molding apparatus of claim 1 in which said heating and cooling coils are both mounted in a single sleeve member.

4. The molding apparatus of claim 1 including resilient means for mounting and spontaneously aligning said tubular molding chamber in the molding apparatus whereby said molding chamber spontaneously aligns with said ramhead as the ramhead moves along the length of the chamber.

5. In molding apparatus which comprises a tubular molding chamber; a ramhead sealingly movable along the length of the interior of said chamber; and fluid pressure means for advancing and retracting said ramhead along said chamber; the improvement comprising, in combination:

hydraulic chamber means; a shaft extending axially from said ramhead into said hydraulic chamber in sealing manner and terminating in a sliding piston within said hydraulic chamber to divide said hydraulic chamber into a pair of variable volume portions positioned on opposed sides of said piston, each portion being connectable by hydraulic flow conduit means to a source of pressurized hydraulic fluid, to permit driven movement of said piston in said chamber; pressure sensing means operably connected to the hydraulic chamber portion which is spaced from said ramhead by said piston; and logic and control means operably connected to said pressure sensing means and pressurized hydraulic fluid source to control the pressure of hydraulic fluid in said spaced chamber portion in a manner responsive to signals from said pressure sensing means; said molding chamber being surrounded by a helical heating coil; temperature measuring means positioned adjacent said molding chamber; and control means for operating said heating coil in a manner responsive to signals from said temperature measuring means; in which said molding chamber is threadedly attached to a base member at one end, the opposed end of the molding chamber carrying a handle member, said handle member defining an annular flange with first, spaced, peripheral, flat areas, said opposed end defining second, spaced, peripheral, flat areas proportioned to enter into longitudinal registry with the first, peripheral, flat areas by proper rotational orientation; said handle member carrying a wrench member which defines third flat areas on an inner surface thereof, said wrench member being proportioned to slide over said flange and opposed end, with the third flat areas overlying the first and second flat areas, whereby said handle can be used to rotate the molding chamber out of threaded attachment with said base member to open the mold.

6. The apparatus of claim 5 in which the opposed end of the molding chamber is removably threadedly attached to said handle member.

7. In molding apparatus which comprises a tubular molding chamber; a ramhead sealingly movable along the length of the interior of said chamber; and fluid pressure means for advancing and retracting said ramhead along said chamber; the improvement comprising, in combination: a hydraulic chamber; a shaft extending axially from said ramhead into said hydraulic chamber in sealing manner and terminating in a sliding piston within said hydraulic chamber to define in said hydraulic chamber a pair of variable volume portions positioned on opposed sides of said piston, each portion being connectable by hydraulic flow conduit means to a source of pressurized hydraulic fluid to permit driven movement of said piston in said chamber; pressure sensing means operably connected to the hydraulic chamber portion which is spaced from said ramhead by said piston; and logic and control means operably connected to said pressure sensing means and pressurized hydraulic fluid source to control the pressure of hydraulic fluid in said spaced chamber portion in a manner responsive to signals from said pressure sensing means; resilient means for mounting and aligning said tubular molding chamber in said molding apparatus, whereby said molding chamber spontaneously aligns with said ramhead as the ramhead moves along the length of said molding chamber; said molding chamber being threadedly attached to a base member at one end, the opposed end of said molding chamber carrying a handle member, said handle member defining an annular flange with first, spaced, peripheral, flat areas, said opposed end defining second, spaced, peripheral, flat areas proportioned to enter into longitudinal registry with the first, peripheral, flat areas by proper rotational orientation; said handle member carrying a wrench member which defines third flat areas on an inner surface thereof, said wrench member being proportioned to slide over said flange and opposed end, with the third flat areas overlying the first and second flat areas, whereby said handle can be used to rotate the molding chamber out of threaded attachment with said base member to open the mold.

8. The molding apparatus of claim 7 in which said molding chamber is surrounded by helical heating and cooling coils mounted in a single sleeve member; temperature measuring means positioned adjacent said molding chamber; and control means for operating at least said heating coil in a manner responsive to signals from said temperature measuring means.

9. The apparatus of claim 8 in which said fluid pressure means comprises a hydraulic fluid pump connected by a third conduit to double acting venting valve means connected to the hydraulic flow conduit means which respectively connect to the variable volume portions, whereby switching of said valve means can cause alternating pressurizing and venting of each of said portions.

10. The apparatus of claim 9 in which said base member is loosely attached to a platform, and supported on wave spring means, to provide the resilient means for mounting said tubular molding chamber and the spontaneous alignment with said ramhead.

11. The apparatus of claim 10 in which the opposed end of the molding chamber is releasably threadedly attached to said handle member.

12. A molding apparatus which comprises a tubular molding chamber, a ramhead sealingly movable along the length of said chamber, and driving means for said ramhead, the improvement comprising, in combination:

resilient means for mounting and aligning said tubular molding chamber in said molding apparatus, whereby said molding chamber spontaneously aligns with said ramhead as the ramhead moves along the length of said chamber, said molding chamber being threadedly attached to a base member at one end, the opposed end of said molding chamber carrying a handle member, said handle member defining an annular flange with first spaced, peripheral, flat areas, said opposed end defining second, spaced peripheral, flat areas proportioned to enter into longitudinal registry with the first, peripheral, flat areas by proper rotational orientation; said handle member carrying a wrench member which defines third flat areas on an inner surface thereof, said wrench member being proportioned to slide over said flange and opposed end, with the third flat areas overlying the first and second flat areas, whereby said handle can be used to rotate the molding chamber out of threaded attachment with said base member to open the mold.

13. The apparatus of claim 12 in which the opposed end of the molding chamber is threadedly attached to said handle member.

14. The apparatus of claim 12 in which said molding chamber is surrounded by helical heating and cooling coils.

15. The apparatus of claim 12 in which said base member is loosely attached to a platform, to permit movement of the base member with the molding chamber as the chamber aligns with the ram head.

16. The molding apparatus of claim 13 in which said molding chamber is surrounded by helical heating and cooling coils which are both mounted in a single sleeve member, said apparatus further including a hydraulic chamber; a shaft extending axially from said ramhead into said hydraulic chamber in sealing manner and terminating in a sliding piston within said hydraulic chamber to divide said hydraulic chamber into a pair of variable volume portions positioned on opposed sides of said piston, each portion being connectable by hydraulic flow conduit means to a source of pressurized hydraulic fluid, to permit driven movement of said piston in said chamber; pressure sensing means operably connected to the hydraulic portion which is spaced from said ramhead by said piston; logic and control means operably connected to said pressure sensing means and pressurized hydraulic fluid source, to control the pressure of hydraulic fluid in said spaced chamber portion in a manner responsive to signals from said pressure sensing means.

17. The apparatus of claim 16 in which temperature measuring means are positioned adjacent said molding chamber; and control means are provided for operating at least said heating coil in a manner responsive to signals from said temperature measuring means.

* * * * *